(12) United States Patent
Hoeffkes et al.

(10) Patent No.: US 6,743,263 B1
(45) Date of Patent: Jun. 1, 2004

(54) METHOD FOR COLORING KERATIN FIBERS

(75) Inventors: Horst Hoeffkes, Duesseldorf (DE); Doris Oberkobusch, Duesseldorf (DE); David Rose, Hilden (DE); Melanie Hitz, Dormagen (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 09/869,171

(22) PCT Filed: Dec. 14, 1999

(86) PCT No.: PCT/EP99/09901

§ 371 (c)(1),
(2), (4) Date: Oct. 31, 2001

(87) PCT Pub. No.: WO00/38629

PCT Pub. Date: Jul. 6, 2000

(30) Foreign Application Priority Data

Dec. 23, 1998 (DE) .................................. 198 59 800

(51) Int. Cl.⁷ ................................................ A61K 7/13
(52) U.S. Cl. ................... 8/405; 8/406; 8/408; 8/409; 8/411; 8/412; 8/421; 8/423; 8/477; 8/550; 8/565; 8/568; 8/573
(58) Field of Search ................ 8/405, 406, 408, 8/409, 411, 412, 421, 423, 477, 550, 565, 568, 573

(56) References Cited

U.S. PATENT DOCUMENTS

| | | | |
|---|---|---|---|
| 4,865,774 A | 9/1989 | Fabry et al. | 252/554 |
| 4,931,218 A | 6/1990 | Schenker et al. | 252/551 |
| 5,176,716 A | 1/1993 | Lorenz et al. | 8/405 |
| 5,294,726 A | 3/1994 | Behler et al. | 554/98 |
| 5,318,599 A | 6/1994 | Lorenz et al. | 8/405 |

FOREIGN PATENT DOCUMENTS

| | | |
|---|---|---|
| DE | 37 23 354 | 1/1989 |
| DE | 37 25 030 | 2/1989 |
| DE | 39 26 344 | 2/1991 |
| DE | 91 05 827 | 8/1991 |
| DE | 41 15 148 | 11/1992 |
| DE | 195 35 340 | 3/1997 |
| DE | 195 39 264 | 4/1997 |
| DE | 196 10 947 | 9/1997 |
| DE | 196 14 303 | 10/1997 |
| DE | 297 02 192 | 6/1998 |
| EP | 0 542 129 | 5/1993 |
| EP | 0 657 157 | 6/1995 |
| EP | 0 657 158 | 6/1995 |
| WO | WO 92/19220 | 11/1992 |

OTHER PUBLICATIONS

The Science of Hair Care, Chapter 7, pp. 235–261, published as vol. 7 of Dermatology, Marcel Dekker Inc., NY/Basel (1986).

The Science of Hair Care, Chapter 8, pp. 263–286, published as vol. 7 of Dermatology, Marcel Dekker, Inc., NY/Basel (1986).

EU Inventory of Cosmetic Ingredients, Colipa, Mar. 1996 on diskette.

*Primary Examiner*—Yogendra Gupta
*Assistant Examiner*—Eisa Elhilo
(74) *Attorney, Agent, or Firm*—Stephen D. Harper; Gregory M. Hill

(57) ABSTRACT

The present invention relates to a composition for coloring keratinaceous fibers and a method of using the same. The composition of the present invention contains (a) at least one pyrimidine derivative and (b) at least one compound selected from an m-phenylene derivative, an m-aminophenol derivative, a pyridine derivative, a resorcinol derivative, a methylenedioxybenzene derivative, or 3,4-diaminobenzoic acid or combinations thereof. The method of the present invention includes applying the coloring composition to keratin-containing fibers and subsequently rinsing the coloring composition from the fibers.

12 Claims, No Drawings

METHOD FOR COLORING KERATIN FIBERS

CROSS REFERENCE TO RELATED APPLICATIONS

This application is a national stage application under 35 U.S.C. § 371 of international application PCT/EP99/09901 filed on Dec. 14, 1999, the international application not being published in English. This application also claims priority under 35 U.S.C. §119 to DE 198 59 800.9, filed on Dec. 23, 1998.

FIELD OF THE INVENTION

The invention relates to an agent for dyeing keratin fibers, in particular human hair, which comprises pyrimidine derivatives in combination with special couplers, to the use of this combination as dyeing component in hair dyeing agents, and to a method of dyeing keratin fibers, in particular human hair.

BACKGROUND OF THE INVENTION

For the dyeing of keratin fibers, e.g. hair, wool or furs, use is generally made either of substantive dyes or oxidation dyes which are formed by oxidative coupling of one or more developer component with one another or with one or more coupler components. Coupler and developer components are also referred to as oxidation dye precursors.

The developer components usually used are primary aromatic amines having a further free or substituted hydroxyl or amino group in the para or ortho position, diaminopyridine derivatives, heterocyclic hydrazones, 4-aminopyrazolone derivatives, and 2,4,5,6-tetraaminopyrimidine and derivatives thereof.

Specific representatives are, for example, p-phenylenediamine, p-toluylenediamine, 2,4,5,6-tetraaminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The coupler components usually used are m-phenylenediamine derivatives, naphthols, resorcinol and resorcinol derivatives, pyrazolones and m-aminophenols. Particularly suitable as coupler substances are α-naphthol, 1,5-, 2,7- and 1,7-dihydroxynaphthaline, 5-amino-2-methylphenol, m-aminophenol, resorcinol, resorcinol monomethyl ether, m-phenylenediamine, 2,4-diaminophenoxyethanol, 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol and 5-methylresorcinol.

German patent application DE-Al-41 15 148 discloses oxidation dyeing agents which, in a cosmetic carrier, comprise a 2,4,5,6-tetraaminopyrimidine or a 6-hydroxy-2,4-triaminopyridine as oxidation base (developer) and a combination of certain green couplers and violet couplers for producing brilliant and washfast black colorations.

With regard to further customary dye components, reference is made specifically to the "Dermatology" series, published by Ch. Culnan, H. Maibach, Verlag Marcel Dekker Inc., New York, Basle, 1986, vol. 7, Ch. Zviak, The Science of Hair Care, chapter 7, pages 248–250 (substantive dyes), and chapter B, pages 264–267 (oxidation dyes), and the "European Inventory of Cosmetic Raw Materials", 1996, published by the European Commission, available in diskette format from the Bundesverband der deutschen Industrie-und Handelsunternehmen für Arzneimittel, Reformwaren und Körperpflegemittel e.V., Mannheim.

Although intensive colorations with good fastness properties can be achieved with oxidation dyes, the development of the color, however, generally takes place under the influence of oxidizing agents, such as, for example, $H_2O_2$, which in some cases can result in damage to the fibers. Furthermore, some oxidation dye precursors or certain mixtures of oxidation dye precursors can occasionally have a sensitizing effect in people with sensitive skin. Although substantive dyes are applied under more moderate conditions, their disadvantage is that the colorations frequently have inadequate fastness properties.

It is an object of the present invention to provide a dyeing agent for keratin fibers, in particular human hair, which is oxidizable by atmospheric oxygen, i.e. is not necessarily dependent on oxidizing agents, such as, for example, $H_2O_2$. The agent should be able to be applied to the fibers in a simple manner and, with regard to depth of color, gray coverage and fastness properties, are at least equal in qualitative terms to otherwise customary oxidation hair dyeing agents. Moreover, the dyeing agents must have no, or only a very low, sensitizing potential. It was a further object to find a dyeing system that allows blue shades to be produced on the keratin fiber by components specifically matched to one another.

SUMMARY OF THE INVENTION

Surprisingly, it has now been found that pyrimidine derivatives in combination with special couplers are highly suitable for the dyeing of keratin fibers, even in the absence of oxidizing agents i.e. in the presence of atmospheric oxygen. They produce colorations with excellent brilliance and depth of color and lead to a wide variety of color shades. However, the use of oxidizing agents should not in principle be excluded here.

The invention provides an agent for the dyeing of keratin fibers, in particular human hair, comprising A) at least one pyrimidine derivative of the general formula I

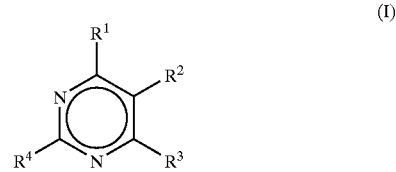

(I)

in which $R^1$, $R^2$, $R^3$ and $R^4$ may be identical or different and are hydrogen, OH, $NH_2$ or a group $NR^5R^6$, in which $R^5$ and $R^6$ may be identical or different and are $C_1$–$C_4$-alkyl, $C_1$–$C_4$-hydroxyalkyl having a primary and/or secondary hydroxyl group, where two of the radicals $R^1$, $R^2$, $R^3$ or $R^4$ together can form an optionally substituted 5- and 6-membered heterocycle containing one or two nitrogen and/or oxygen atom(s) in the molecule, with the proviso that at least two of the radicals $R^1$, $R^2$, $R^3$ or $R^4$ are a group $NH_2$ and/or $NR^5R^6$, B) at least one compound chosen from the group consisting of
(a) m-phenylene derivatives of the formulae II and III

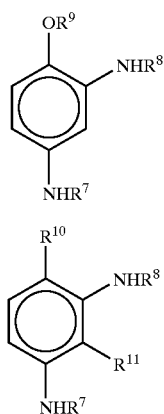

in which $R^7$ and $R^8$ may be identical or different and are hydrogen, $C_1$–$C_4$-alkyl or $C_1$–$C_4$-hydroxyalkyl, $R^9$ is $C_1$–$C_4$-hydroxyalkyl or a radical of the general formula IV

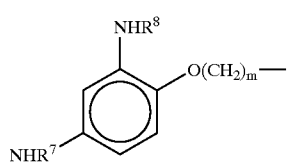

in which $R^7$ and $R^8$ are as defined above and m is an integer from 1 to 4,
$R^{10}$ is hydrogen or a radical of the general formula V

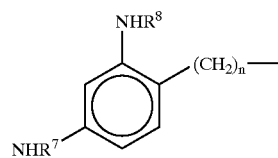

in which $R^7$ and $R^9$ are as defined above and n is an integer from 1 to 4,
$R^{11}$ is hydrogen, $C_1$–$C_4$-alkyl or $C_1$–$C_4$-hydroxyalkyl,
(b) m-aminophenol derivatives

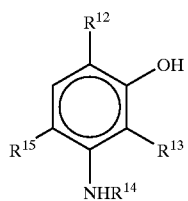

in which $R^{12}$ is hydrogen or $C_1$–$C_4$-alkyl,
$R^{13}$ is hydrogen, fluorine, chlorine, $OCH_3$ or $C_1$–$C_4$-alkyl,
$R^{14}$ is hydrogen, $C_1$–$C_4$-alkyl, $C_1$–$C_4$-hydroxyalkyl or $OCF_3$,
$R^{15}$ is hydrogen, fluorine, chlorine or $OCH_3$,
with the provisos that $R^{12}$, $R^{13}$, $R^{14}$ and $R^{15}$ are not hydrogen at the same time and that, if $R^{12}$ is methyl, $R^{13}$, $R^{14}$ and $R^{15}$ are not hydrogen at the same time,
(c) pyridine derivatives of the formulae VII and VIII

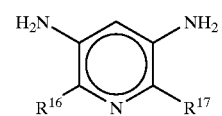

in which $R^{16}$ and $R^{17}$ may be identical or different and are fluorine, chlorine or $OCH_3$,

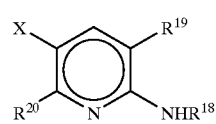

in which $R^{18}$ is hydrogen, $C_1$–$C_4$-alkyl or $C_1$–$C_4$-hydroxyalkyl,
$R^{19}$ is OH or $NH_2$,
$R^{20}$ is hydrogen, $C_1$–$C_4$-alkoxy or $NH_2$,
X is hydrogen or $OCH_3$,
with the provisos that, if $R^{19}$ is $NH_2$, $R^{18}$ and $R^{20}$ are not $C_1$–$C_4$-alkyl or methoxy respectively at the same time, and if $R^{18}$ is hydrogen, $R^{19}$ and $R^{20}$ are not OH or hydrogen respectively at the same time,
(d) resorcinol derivatives of the formula IX

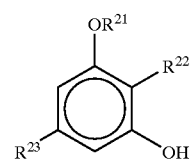

in which $R^{21}$, $R^{22}$ and $R^{23}$ may be identical or different and are hydrogen, $C_1$–$C_4$-alkyl or $C_1$–$C_4$-hydroxyalkyl,
with the provisos that $R^{21}$, $R^{22}$ and $R^{23}$ are not hydrogen at the same time, if $R^{21}$ and $R^{23}$ are hydrogen, $R^{22}$ is not methyl, and if $R^{21}$ is methyl, $R^{22}$ and $R^{23}$ are not hydrogen at the same time,
(e) methylenedioxybenzene derivatives of the formula X

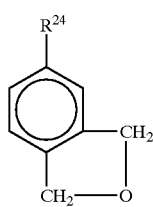

in which $R^{24}$ is OH, $NH_2$ or $NHR^{25}$, in which $R^{25}$ is $C_1$–$C_4$-alkyl or $C_1$–$C_4$-hydroxyalkyl, and
(f) 3,4-diaminobenzoic acid.

DETAILED DESCRIPTION OF THE INVENTION

Keratin fibers are to be understood as meaning wool, furs, feathers and, in particular, human hair. In principle, however, the dyes according to the invention may also be used for the dyeing of other natural fibers, such as, for example, cotton, jute, sisal, linen or silk, modified natural fibers, such as, for example, regenerated cellulose, nitro-, alkyl- or hydroxyalkyl- or acetylcellulose, and synthetic fibers, such as, for example, polyamide, polyacrylonitrile, polyurethane and polyester fibers.

The pyrimidine derivatives of the formula I used according to the invention are preferably chosen from the group consisting of 4-hydroxy-2,5,6-triaminopyrimidine, 2-hydroxy-2,5,6-triaminopyrimidine, 2,4,5,6-tetraaminopyrimidine, 5,6-diamino-2,4-dihydroxypyrimidine, 2,4-diamino-5,6-dihydroxypyrimidine, 4-dimethylamino-2,5,6-tetraminopyrimidine. Particular preference is given to using 2,4,5,6-tetraaminopyrimidine, 4-dimethylamino-2,5,6-tetraminopyrimidine, 4-hydroxy-2,5,6-triaminopyrimidine and 5,6-diamino-2,4-dihydroxypyrimidine.

These substances are known from the literature or are available commercially.

The aforementioned pyrimidine derivatives of the formula I are preferably used in the agents according to the invention in an amount of from 0.03 to 65 mmol, in particular from 1 to 40 mmol, based on 100 g of the total dyeing agent.

Of the compounds of the formula VIII, preference is given to those in which X is hydrogen.

Couplers of component B are preferably chosen from the group 1,3-bis(2,4-diaminophenoxypropane), 1,3-bis(2,4-diaminophenylpropane), 2,4-diaminophenoxyethanol, 2,6-bis(2'-hydroxyethylamino)toluene, 3-amino-2-chloro-6-methylphenyl, 5-amino-4-chloro-2-methylphenol, 2,9-dichloro-3-aminophenol, 3,5-diamino-2,6-dimethoxypyridine, 5-methylresorcinol, 2,5-dimethylresorcinol, 3,4-methylenedioxyphenol, 3,4-methylenedioxyaniline, N-(2-hydroxyethyl)-3,4-methylenedioxyaniline and any mixtures of the above.

The aforementioned compounds of component B can be used in an amount of, in each case, 0.03 to 65 mmol, in particular 1 to 40 mmol, in each case based on 100 g of the total dyeing agent.

In all of the dyeing agents it is also possible to use two or more different pyrimidine derivatives of the formula I together; likewise, it is also possible to use two or more different compounds of component B together. This embodiment also covers the use of substances which represes reaction products of pyrimidine derivatives of the formula I with said compounds of component B.

The color shades can also be further varied and intensified if one or more compounds chosen from 5,6-dihydroxyindole and its N-substituted $C_1$–$C_4$-alkyl and $C_1$–$C_4$-hydroxyalkyl derivatives, 5,6-dihydroxyindoline and its N-substituted $C_1$–$C_4$-alkyl and $C_1$–$C_4$-hydroxyalkyl derivatives and the compounds known as developers, chosen from the group consisting of p-phenylenediamine, p-tolylenediamine, p-aminophenol, 4,4'-diaminodiphenylamine, 1,10-bis(2,5-diaminophenyl)-1,4,7,10-tetraoxydecane, 2, (2'-hydroxyethyl)-p-phenylenediamine, 2,6-dichloro-4-aminophenol, N,N-bis(2'-hydroxyethyl)-p-phenylenediamine, 3-methyl-4-aminophenol, 2-aminomethyl-4-aminophenol, 5-aminosalicylic acid, bis (2-hydroxy-5-aminophenyl)methane and 2-(2,5-diaminophenoxy)ethanol are added to the agent according to the invention.

A further preferred developer component is 4-amino-2-((diethylamino)methyl)phenol.

Particularly preferred developer components are, for example, p-phenylenediamine, p-tolylenediamine, 1,10-bis(2,5-diaminophenyl)-1,4,7,10-tetraoxydecane, 2, (2'-hydroxyethyl)-p-phenylenediamine, 2,6-dichloro-4-aminophenol, N,N-bis(2'-hydroxyethyl)-p-phenylenediamine, 3-methyl-4-aminophenol, 2-aminomethyl-4-aminophenol, 4-amino-2-((diethylamino) methyl)phenol and bis(2-hydroxy-5-aminophenyl)methane.

In a further preferred embodiment, activated carbonyl compounds and further substances known as developers or couplers are added to the combination according to the invention of components A and B to further modify the color shades.

Examples of activated carbonyl compounds are isatin, 5-chloroisatin, 5-bromoisatin, 6-bromoisatin, 5-nitroisatin, N-hydroxymethylisatin, N-allylisatin, 5-isatinsulfonic acid Na salt, glutaconaldehyde tetrabutylammonium salt, tribase aldehyde, malonaldehyde bis(dimethyl acetal), 4-hydroxy-3-methoxycinnanaldehyde, 1-piperidinomethylisatin, 1-diethylaminomethylisatin, glutaconaldehyde Na salt, 5-N-methylanilinopentadienyl, 2-chloro-3-hydroxy-methylene-1-cyclohexene 1-aldehyde, N-(5-anilino-2,4-pentanedien-1-ylidene)anilinium chloride, trans-p-(2-furyl)acrolein, 2-nitro-1,3-indanedione, dehydroascorbic acid, 2-acetyl-1, 3-cyclohexanedione, 7-dimethylamino-2,4,6-heptatrienylidene dimethylammonium perchlorate and 4-formyl-1-methylpyridinium benzenesulfonate.

Examples of couplers which may additionally be present are 3-amino-2-methylamino-6-methoxypyridine, 2-amino-4-(2'-hydroxyethylamino)anisole, α-naphthol, resorcinol, resorcinol monomethyl ether, 4-chlororesorcinol, 2-methylresorcinol, m-aminophenol, 3-N,N-dimethylaminophenol, 5-amino-2-methoxyphenol, 5-amino-2-methylphenol, 3-amino-2,4-dimethylphenol, 3-(N-cyclopentyl)aminophenol, 1,5-, 1,7-, 2,7-dihydroxynaphthalenes, o-aminophenol, 6-hydroxybenzomorpholine, 1-phenyl-3-methylpyrazol-5-one, 2-amino-6-methylphenol, 2,6-dihydroxy-3,4-dimethylpyridine, 4-hydroxyindole, 6-hydroxyindole, 7-hydroxyindole, 4-aminoindole and 2,4-diamino-5-methylphenetole.

The dyeing agent according to the invention represents an air-oxidizable system. In this connection, it is possible to dispense with additional oxidizing agents, e.g. $H_2O_2$. In some circumstances, however, it may be desirable to add hydrogen peroxide or other oxidizing agents, such as peroxydisulfate or percarbonate, to the agents according to the invention to achieve shades which are paler than keratin fibers to be dyed. Furthermore, in some circumstances, it is possible, in the absence of oxidizing agents, i.e. whether atmospheric oxygen or hydrogen peroxide is used, to establish different color shades. Oxidizing agents are generally used in an amount of from 0.01 to 6% by weight, based on the use solution. An oxidizing agent preferred for human hair is $H_2O_2$.

Furthermore, it is possible to carry out the oxidation using enzymes. Here, the enzymes can be used either to generate oxidizing percompounds, and to intensify the effect of a small amount of oxidizing agent present. Examples of enzymatic processes are the use of laccases and the intensification of the effect of small amounts (e.g. 1% and less, based on the total agent) of hydrogen peroxide by peroxidases.

In a preferred embodiment, the dyes according to the invention comprise, for the further modification of the color shades, in addition to the compounds present according to the invention, additionally customary substantive dyes, e.g. from the group of nitrophenylenediamines, nitroaminophenols, anthraquinones or indophenols, such as, for example, the compounds known under the international designations or trade names HC Yellow 2, HC Yellow 4, HC Yellow 6, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16 and Basic Brown 17, and also picramic acid, 2-amino-6-chloro-4-nitrophenol, 4-amino-2-nitrodiphenylamine-2'-carboxylic acid, 6-nitro-1,2,3,4-tetrahydroquinoxaline, 4-N-ethyl-1,4-bis(2'-hydroxyethylamino)-2-nitrobenzene hydrochloride and 1-methyl-3-nitro-4-(2'-hydroxyethyl)aminobenzene. The inventive agents according to this embodiment preferably comprise the substantive dyes in an amount of from 0.01 to 20% by weight, based on the total dyeing agent.

Furthermore, the preparations according to the invention can also comprise naturally occurring dyes such as, for example, henna red, henna neutral, henna black, camomile blossom, sandalwood, black tea, buckthorn bark, sage, logwood, madder root, catechu, sedre and alkanna root.

It is not necessary for the oxidation dye precursors or the optionally present substantive dyes to each represent uniform compounds. Rather, it is possible that, as a result of the preparation processes for the individual dyes, further components are present in minor amounts in the dyeing agents according to the invention, provided these do not adversely impair the dyeing result, or have to be excluded for other reasons, e.g. toxicological reasons.

The dyeing agents according to the invention produce intensive colorations even at physiologically compatible temperatures of less than 45° C. They are therefore particularly suitable for the dyeing of human hair. For use on human hair, the dyeing agents can usually be incorporated into a hydrous cosmetic carrier. Suitable hydrous cosmetic carriers are e.g. creams, emulsions, gels and also surfactant-containing foaming solutions such as e.g. shampoos or other preparations which are suitable for use on the keratin. fibers. If necessary, it is also possible to incorporate the dyeing agents into anhydrous carriers.

Furthermore, the dyeing agents according to the invention can comprise all active ingredients, additives and auxiliaries known in such preparations. In many cases, the dyeing agents comprise at least one surfactant, where, in principle, both anionic and also zwitterionic, ampholytic, nonionic and cationic surfactants are suitable. However, in many cases it has proven advantageous to choose the surfactants from anionic, zwitterionic or nonionic surfactants.

Suitable anionic surfactants in preparations according to the invention are all anionic surface-active substances suitable for use on the human body. These are characterized by a solubilizing anionic group, such as, for example, a carboxylate, sulfate, sulfonate or phosphate group and a lipophilic alkyl group having about 10 to 22 carbon atoms. Additionally, glycol or. polyglycol ether groups, ester, ether and amide groups and hydroxyl groups may be present in the molecule. Examples of suitable anionic surfactants are, in each case in the form of the sodium, potassium or ammonium and the mono-, di- and trialkanolammonium salts having 2 or 3 carbon atoms in the alkanol group, linear fatty acids having 10 to 22 carbon atoms (soaps)

ether carboxylic acids of the formula R—O—(CH$_2$—CH$_2$O)$_x$—CH$_2$—COOH, in which R is a linear alkyl group having 10 to 22 carbon atoms and x=0 or 1 to 16, acyl sarcosides having 10 to 18 carbon atoms in the acyl group, acyl taurides having 10 to 18 carbon atoms in the acyl group, acyl isethionates having 10 to 18 carbon atoms in the acyl group, sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups, linear alkanesulfonates having 12 to 18 carbon atoms, linear alpha-olefinsulfonates having 12 to 18 carbon atoms, alpha-sulfo fatty acid methyl esters of fatty acids having 12 to 18 carbon atoms, alkyl sulfates and alkylpolyglycol ether sulfates of the formula R—O(CH$_2$—CH$_2$O)$_x$—SO$_3$H, in which R is a preferably linear alkyl group having 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids having 12 to 24 carbon atoms and 1 to 6 double bonds according to DE-A-39 26 344, esters of tartaric acid and citric acid with alcohols, which represent addition products of approximately 2 to 15 molecules of ethylene oxide and/or propylene oxide to fatty alcohols having 8 to 22 carbon atoms.

Preferred anionic surfactants are alkyl sulfates, alkylpolyglycol ether sulfates and ether carboxylic acids having 10 to 18 carbon atoms in the alkyl group and up to 12 glycol ether groups in the molecule, and in particular salts of saturated and in particular unsaturated C$_8$–C$_{22}$-carboxylic acids, such as oleic acid, stearic acid, isostearic acid and palmitic acid.

Zwitterionic surfactants is the term used for those surface-active compounds which carry at least one quaternary ammonium group and at least one —COO$^{(-)}$— or —SO$_3^{(-)}$ group in the molecule. Particularly suitable zwitterionic surfactants are the betaines, such as the N-alkyl-N,N-dimethylammonium glycinates, for example the cocoalkyldimethylammonium glycinate, N-acyl-amminopropyl-N,N-dimethylammonium glycinates, for example the cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethylglycinate. A preferred zwitterionic surfactant is the fatty acid amide derivative known under the CTFA name Cocamidopropyl Betaine.

Ampholytic surfactants are understood as meaning those surface-active compounds which, apart from a C$_{8-18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkylaminodipropionic acids, N-hydroxyethyl-N-alkylamidopropylglycines, N-alkyltaurines, N-alkylsarcosines, 2-alkylaminopropionic acids and alkylam inoacetic acids having in each case about 8 to 18 carbon atoms in the alkyl group. Particularly preferred ampholytic surfactants are N-cocoalkylaminopropionate,, cocoacylaminoethylaminopropionate and $C_{12-18}$-acylsarcosine.

Nonionic surfactants comprise, as hydrophilic group, e.g. a polyol group, a polyalkylene glycol ether group or a combination of polyol and polyglycol ether group. Such compounds are, for example,

- addition products of 2 to 30 mol of ethylene oxide and/or 0 to 5 mol of propylene oxide to linear fatty alcohols having 8 to 22 carbon atoms, to fatty acids having 12 to 22 carbon atoms and to alkyl phenols having 8 to 15 carbon atoms in the alkyl group,
- $C_{12-22}$-fatty acid mono- and diesters of addition products of from 1 to 30 mol of ethylene oxide to glycerol,
- $C_{8-22}$-alkyl mono- and oligoglycosides and ethoxylated analogs thereof,
- addition products of from 5 to 60 mol of ethylene oxide to castor oil and hydrogenated castor oil,
- addition products of ethylene oxide to sorbitan fatty acid esters
- addition products of ethylene oxide to fatty acid alkanolamides.

Examples of the cationic surfactants to be used in the hair-treatment agents according to the invention are, in particular, quaternary ammonium compounds. Preference is given to ammonium halides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further cationic surfactants which can be used according to the invention are the quaternized protein hydrolysates.

Likewise suitable for the invention are cationic silicone oils, such as, for example, the commercially available products Q2-7224 (manufacturer: Dow Corning; a stabilized trimethylsilylamodimethicone), Dow Corning 949 emulsion (comprising a hydroxylamino-modified silicone, which is also referred to as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80).

Alkylamidoamines, in particular fatty acid amidoamines, such as stearylamidopropyldimethylamine obtainable under the name Tego Amid®S 18, are distinguished not only by. a good conditioning action, but specifically by their good biodegradability.

Likewise very biodegradable are quaternary ester compounds, "ester quats", such as the. methylhydroxyalkyldialkoyloxyalkylammonium methosulfates sold under the trade name Stepantex®.

An example of a quaternary sugar derivative which: can be used as cationic surfactant is the commercial product Glucquat® 100, according to CTFA nomenclature a "Lauryl Methyl Gluceth-10 Hydroxypropyl Dimonium Chloride".

The compounds containing alkyl groups which are used as surfactants may each be uniform substances. However, it is generally preferred to start from natural vegetable or animal raw materials for the preparation of these substances, thus giving substance mixtures having varying alkyl chain lengths depending on the respective raw material.

In the case of the surfactants which represent addition products of ethylene and/or propylene oxide to fatty alcohols or derivatives of these addition products, it is possible to use either products with a "normal" homolog distribution, or those with a narrowed homolog distribution. "Normal" homolog distribution is understood as meaning here mixtures of homologs obtained during the reaction of fatty alcohol and alkylene oxide using alkali metals, alkali metal hydroxides or alkali metal alkoxides as catalysts. Narrowed homolog distributions are, by contrast, obtained if, for example, hydrotalcites, alkaline earth metal salts of ether carboxylic acids, alkaline earth metal oxides, hydroxides or alkoxides are used as catalysts. The use of products having narrowed homolog distribution may be preferable.

Further active ingredients, auxiliaries and additives are, for example,

- nonionic polymers such as, for example, vinyloyrrolidone/vinyl acrylate copolymers, polyvinylpyrrolidone and vinylpyrrolidone/vinyl acetate copolymers and polysiloxanes,
- cationic polymers, such as quaternized cellulose ethers, polysiloxanes containing quaternary groups, dimethyldiallylammonium chloride polymers, acrylamide-dimethyldiallylammonium chloride copolymers, dimethylaminoethyl methacrylatevinylpyrrolidone copolymers quaternized with diethyl sulfate, vinylpyrrolidoneimidazolinium methochloride copolymers and quaternized polyvinyl alcohol,
- zwitterionic and amphoteric polymers such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
- anionic polymers such as, for example, polyacrylic acids, crosslinked polyacrylic acids, vinyl acetate/crotonic acid copolymers, vinylpyrrolidonelvinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers,
- thickeners, such as agar agar, guar gum, alginates, xanthan gum, gum arabic, karaya gum, carob bean flour, linseed gums, dextrans, cellulose derivatives, e.g. methylcellulose, hydroxyalkylcellulose and carboxymethylcellulose, starch fractions and derivatives such as amylose, amylopectin and dextrins, clays such as, for example, bentonite or fully synthetic hydrocolloids such as, for example, polyvinyl alcohol,
- structurants, such glucose and maleic acid,
- hair-conditioning compounds, such as phospholipids, for example soya lecithin, egg lecithin and cephalins, and silicone oils,
- protein hydrolysates, in particular elastin, collagen, keratin, milk protein, soya protein and wheat protein hydrolysates, condensation products thereof with fatty acids, and quaternized protein hydrolysates,
- perfume oils, dimethyl isosorbide and cyclodextrins,
- solubility promoters, such as ethanol, isopropanol, ethylene glycol, propylene glycol, glycerol and diethylene glycol,
- antidandruff agents, such as Piroctone Olamine and Zinc Omadine,
- further substances for adjusting the pH,
- active ingredients, such as panthenol, pantothenic acid, allantoin, pyrrolidonecarboxylic acids and salts thereof, plant extracts and vitamins,
- cholesterol,
- light protection agents, consistency regulators, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration substances, such as glycerol, propylene glycol monoethyl ether, carbonates, hydrogencarbonates, guanidines, ureas, and primary, secondary and tertiary phosphates, imidazoles, tannins, pyrrole, opacifiers, such as latex, pearlizing agents, such as ethylene glycol mono- and distearate, propellants, such as propane/butane mixtures, $N_2O$, dimethyl ether, $CO_2$ and air, and antioxidants.

The constituents of the hydrous carrier are used for the preparation of the dyeing agents according to the invention in amounts customary for this purpose; e.g. emulsifiers are used in concentrations of from 0.5 to 30% by weight, and thickeners are used in concentrations of from 0.1 to 25% by weight, of the total dyeing agent.

For the dyeing result, it may be advantageous to add ammonium or metal salts to the dyeing agents. Suitable metal salts are e.g. formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminum, manganese, iron, cobalt, copper or zinc, preference being given to sodium acetate, lithium bromide, calcium bromide, calcium gluconate, zinc chloride, zinc sulfate, magnesium chloride, magnesium sulfate, ammonium carbonate, chloride and acetate. These salts are preferably present in an amount of from 0.03 to 65 mmol, in particular from 1 to 40 mmol, based on 100 g of the total dyeing agent.

The pH of the ready-to-use dyeing preparations is usually between 2 and 11, preferably between 5 and 9.

The present invention further provides for the use of a combination of

A) at least one pyrimidine derivative of the general formula I

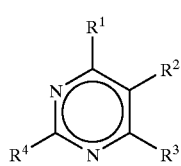

(I)

in which $R^1$, $R^2$, $R^3$ and $R^4$ may be identical or different and are hydrogen, OH, $NH_2$ or a group $NR^5R^6$, in which $R^5$ and $R^6$ may be identical or different and are $C_1$–$C_4$-alkyl, $C_1$–$C_4$-hydroxyalkyl having a primary and/or secondary hydroxyl group, where two of the radicals $R^1$, $R^2$, $R^3$ or $R^4$ together can form an optionally substituted 5- and 6-membered heterocycle containing one or two nitrogen and/or oxygen atom(s) in the molecule, with the proviso that at least two of the radicals $R^1$, $R^2$, $R^3$ or $R^4$ are a group $NH_2$ and/or $NR^5R^6$, B) at least one compound chosen from the group consisting of the (a) m-phenylenediamine derivatives of the general formulae II or III, (b) m-aminophenol derivatives of the general formula VI, (c) pyridine derivatives of the formulae VII or VIII, (d) resorcinol derivatives of the formula IX, (e) methyldioxybenzene derivatives of the formula X or (f) 3,4-diaminobenzoic acid, which are shown above, for dyeing keratin fibers.

The present invention also further provides a method of dyeing keratin fibers, in particular human hair, in which a dyeing agent comprising A) at least one pyrimidine derivative of the general formula I,

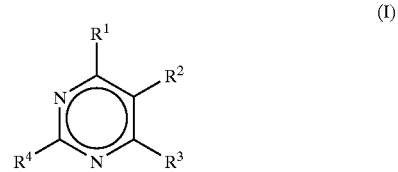

(I)

in which $R^1$, $R^2$, $R^3$ and $R^4$ may be identical or different and are hydrogen, OH, $NH_2$ or a group $NR^5R^6$, in which $R^5$ and $R^6$ may be identical or different and are $C_1$–$C_4$-alkyl, $C_1$–$C_4$-hydroxyalkyl having a primary and/or secondary hydroxyl group, where two of the radicals $R^1$, $R^2$, $R^3$ or $R^4$ together can form an optionally substituted 5- and 6-membered heterocycle containing one or two nitrogen and/or oxygen atom(s) in the molecule, with the proviso that at least two of the radicals $R^1$, $R^2$, $R^3$ or $R^4$ are a group $NH_2$ and/or $NR^5R^6$, B) at least one compound chosen from the group consisting of the (a) m-phenylenediamine derivatives of the general formulae II or III, (b) m-aminophenol derivatives of the general formula VI, (c) pyridine derivatives of the formulae VII or VIII, (d) resorcinol derivatives of the formula IX, (e) methyldioxybenzene derivatives of the formula X or (f) 3,4-diaminobenzoic acid, and customary cosmetic ingredients, is applied to the keratin fibers, left on the fibers for a while, usually about 30 minutes, and then rinsed out again or washed out using a shampoo.

The pyrimidine derivatives of the formula I and the compounds of component B can either be applied to the hair simultaneously or one after the other, it being unimportant which of the two components is applied first. If it is necessary to achieve a certain color shade, any oxidizing agent used is also applied. in this stage together with the other components, or subsequently. The optionally present ammonium or metal salts may be added to the first or the second component. There may be an interval of up to 30 minutes. between application of the first component- and that of the second component. Pretreatment of the fibers with the salt solution is also possible.

EXAMPLES

Hair dyeing agents according to the invention were in the form of a hair dyeing cream emulsion of the composition given in Table 1.

TABLE 1

| Component | 1 | 2 | 3 | 4 | 5 | 6 | 7 |
|---|---|---|---|---|---|---|---|
| | % by wt. | | | | | | |
| $C_{12}$–$C_{14}$-fatty alcohol + 2 EO sulfate, Na salt, 28% strength solution | 20.0 | 20.0 | 20.0 | 20.0 | 20.0 | 20.0 | 20.0 |
| Cocoamidopropyl-betaine, 30% strength | 12.5 | 12.5 | 12.5 | 12.5 | 12.5 | 12.5 | 12.5 |
| $C_{10}$–$C_{18}$ fatty alcohol | 2.0 | 2.0 | 2.0 | 2.0 | 2.0 | 2.0 | 2.0 |
| Tallow fatty alcohol | 8.5 | 8.5 | 8.5 | 8.5 | 8.5 | 8.5 | 8.5 |
| $C_{16}$–$C_{18}$ fatty alcohol + 20 EO | 0.75 | 0.75 | 0.75 | 0.75 | 0.75 | 0.75 | 0.75 |
| Ammonium sulfate | 0.1 | 0.1 | 0.1 | 0.1 | 0.1 | 0.1 | 0.1 |
| Sodium sulfate | 0.1 | 0.1 | 0.1 | 0.1 | 0.1 | 0.1 | 0.1 |
| 4-Hydroxy-2,5,6-triaminopyrimidine sulfate | 2.4 | 2.4 | 2.4 | 2.4 | 2.4 | 2.4 | 2.4 |
| 2,4-Diaminophenoxyethanol dihydrochloride | 2.4 | — | — | — | — | — | — |
| 3,5-Diamino-2,6-dimethoxypyridine dihydrochloride | — | 2.4 | — | — | — | — | — |
| 1,3-bis(2,4-Diaminophenoxy)propane tetrahydrochloride | — | — | 4.7 | 2.12 | 1.18 | — | — |
| N-Allylisatin | — | — | — | 0.19 | 0.94 | — | — |
| 1,10-bis(2,5-Diaminophenyl)-1,4,7-10-tetraoxydecane tetrahydrochloride | — | — | — | 1.02 | 5.1 | — | — |
| 3-Amino-2-chloro-6-methylphenol | — | — | — | — | — | 1.58 | — |
| 3,4-Methylenedioxyphenol | — | — | — | — | — | — | 1.38 |
| Water | ad 100 | | | | | | |

The individual constituents were mixed together at 70° C. and, after cooling, adjusted to a pH of 9.5 with NaOH.

Using the compositions given in Table 1, colorations were carried out using $H_2O_2$ as oxidizing agent and without oxidizing agent, i.e. by air oxidation.

For the oxidative development of the coloration using $H_2O_2$, the compositions shown in Table 1 were mixed with 12% strength hydrogen peroxide in the ratio 1:1. In the case of air oxidation, the compositions shown in Table 1 were mixed with water prior to use in the ratio 1:1.

The application mixture was applied to approximately 15 cm-long tresses of standardized, 90% gray human hair which has not been pretreated in any particular way, and left there for 30 minutes at 27° C. When the dyeing process was complete, the hair was rinsed, washed with a customary shampoo and then dried. The coloring results are shown in Table 2.

TABLE 2

| Formulation No. | Color shade | |
|---|---|---|
| | $H_2O_2$ oxidation | Air oxidation |
| 1 | Deep blue-violet | Deep blue-violet |
| 2 | Reddish mid-brown | Reddish mid-brown |
| 3 | Mid-dark brown | Mid-dark brown |
| 4 | — | Dark brown |
| 5 | — | Black |
| 6 | Gray magenta | Rich Bordeaux |
| 7 | Pale orange | Sand-colored |

The dyeing results show that the agents according to the invention produce excellent coloring results both with and without the addition of oxidizing agents. Similar colorations are obtained if, in example 7, the enzyme system glucose-oxidase/glucose/peroxidase or the enzyme system uricase/uric acid/peroxidase is used as oxidizing agent at pH 8.5.

What is claimed is:

1. A method of coloring keratin fibers comprising applying to keratin fibers a coloring composition formed from components comprising A, at least one pyrimidine derivative of formula I

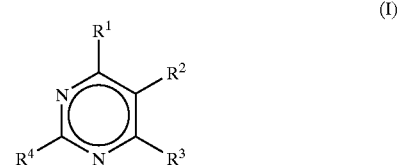

(I)

wherein $R^1$, $R^2$, $R^3$ and $R^4$ are, independently of one another, selected from hydrogen, an OH group, a $NH_2$ group, or a $NR^5R^6$ group, wherein $R^5$ and $R^6$ are independently selected from a $C_1$ to $C_4$ alkyl group, or a $C_1$ to $C_4$ hydroxyalkyl group having one or more hydroxyl groups that are primary, secondary or combinations thereof, or where two of the $R^1$, $R^2$, $R^3$ or $R^4$ substituents together form a 5 or 6 member, optionally substituted, heterocycle ring containing one or two nitrogen atoms, or one or two oxygen atoms or a combination of both in the heterocycle ring, with the proviso that at least two of the $R^1$, $R^2$, $R^3$ or $R^4$ substituents are a $NH_2$ group or $NR^5R^6$ group, and B at least one Compound selected from a m-phenylene derivatives of formula II or III

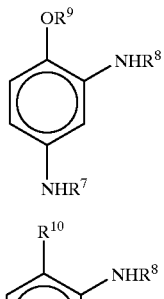

(II)

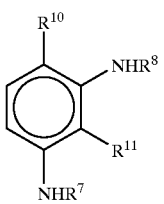

(III)

wherein $R^7$, $R^8$ and $R^{11}$ are independently from one another hydrogen, a $C_1$ to $C_4$ alkyl group or a $C_1$ to $C_4$ hydroxyalkyl group, $R^9$ is a $C_1$ to $C_4$ hydroxyalkyl group or a radical of formula IV

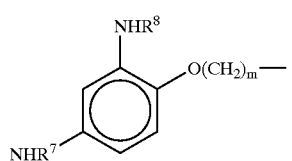

(IV)

in which $R^7$ and $R^8$ are defined as above and m is an integer from 1 to 4, and $R^{10}$ is hydrogen or a radical of formula V

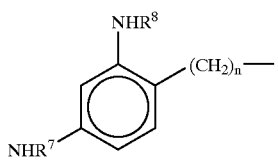

(V)

in which $R^7$ and $R^8$ are as defined above and n is an integer from 1 to 4, b. m-aminophenol derivatives of formula (VI)

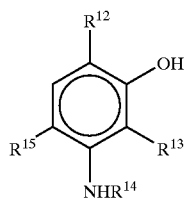

(VI)

wherein $R^{12}$ is hydrogen or a $C_1$ to $C_4$ alkyl group, $R^{13}$ is hydrogen, fluorine, chlorine, an $OCH_3$ group or a $C_1$ to $C_4$ alkyl group, $R^{14}$ is hydrogen, a $C_1$ to $C_4$ alkyl group, a $C_1$ to $C_4$ hydroxyalkyl group or an $OCF_3$ group, $R^{15}$ is hydrogen, fluorine, chlorine or an $OCH_3$ group, with the provisos that $R^{12}$, $R^{13}$, $R^{14}$ and $R^{15}$ are not hydrogen at the same time, and that, if $R^{12}$ is methyl, $R^{13}$, $R^{14}$ and $R^{15}$ are not hydrogen at the same time, c. pyridine derivatives of formula VII or VIII

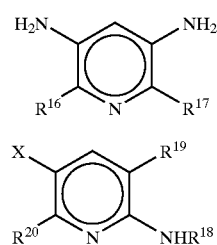

(VII)

(VIII)

wherein $R^{16}$ and $R^{17}$ are independently fluorine, chlorine or an $OCH_3$ group, $R^{18}$ is hydrogen, a $C_1$ to $C_4$ alkyl group or a $C_1$ to $C_4$ hydroxyalkyl group, $R^{19}$ is an OH group or $NH_2$ group, $R^{20}$ is hydrogen, a $C_1$ to $C_4$ alkoxy group or a $NH_2$ group, X is hydrogen or an $OCH_3$ group, with the provisos that, if $R^{19}$ is $NH_2$, $R^{18}$ and $R^{20}$ are not a $C_1$ to $C_4$ alkyl group and a methoxy group, respectively, at the same time, and if $R^{18}$ is hydrogen, $R^{19}$ and $R^{20}$ are not an OH group and hydrogen, respectively, at the same time, d. resorcinol derivatives of formula IX

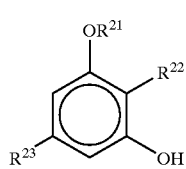

(IX)

wherein $R^{21}$, $R^{22}$ and $R^{23}$ are independently from one another hydrogen, a $C_1$ to $C_4$ alkyl group or a $C_1$ to $C_4$ hydroxyalkyl group, with the provisos that $R^{21}$, $R^{22}$ and $R^{23}$ are not hydrogen at the same time, $R^{22}$ is not methyl if $R^{21}$ and $R^{23}$ are hydrogen, and $R^{22}$ and $R^{23}$ are not hydrogen at the same time if $R^{21}$ is methyl, e. methylenedioxybenzene derivatives of formula X

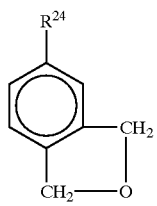

(X)

wherein $R^{24}$ is an OH group, a $NH_2$ group or a $NHR^{25}$ group, in which $R^{25}$ is a $C_1$ to $C_4$ alkyl group or a $C_1$ to $C_4$ hydroxyalkyl, or f. 3,4-diaminobenzoic acid, and
combinations thereof; and C. oxidatively developing the coloring composition using atmospheric oxygen, an enzyme containing system, or combinations thereof as the sole oxidizing agent.

2. The method of claim 1 wherein the pyrimidine derivative is 4-hydroxy-2,5,6-triaminopyrimidine, 2-hydroxy-2,5,6-triaminopyrimidine, 2,4,5,6-tetraaminopyrimidine, 5,6-diamino-2,4-hydroxypyrimidine, 2,4-diamino-5,6-dihydroxypyrimidine, or 4-methylamino-2,5,6-tetraminopyrimidine, or combinations thereof.

3. The method of claim 2 wherein the pyrimidine derivative is 2,4,5,6-tetraaminopyrimidine.

4. The method of claim 2 wherein the pyrimidine derivative is present in the coloring composition in an amount of from 0.03 mmol to 65 mmol, based on 100 g of the coloring composition as a whole.

5. The method of claim 1 wherein at least one of $R^7$ and $R^8$ of the Formula III is a $C_1$ to $C_4$ alkyl group or a $C_1$ to $C_4$ hydroxyalkyl group, and wherein $R^{20}$ of the Formula VIII is hydrogen or a $C_1$ to $C_4$ alkoxy group.

6. The method of claim 1 wherein the component B comprises 1,3-bis(2,4-diaminophenoxypropane), 1,3-bis(2,4-diaminophenylpropane), 2,4-diaminophenoxyethanol, 2,6-bis(2'-hydroxyethylamino)toluene, 3-amino-2-chloro-6-methylphenol, 5-amino-4-chloro-2-methylphenol, 2,4-dichloro-3-aminophenol, 3,5-diamino-2,6-dimethoxypyridine, 5-methylresorcinol, 2,5-dimethylresorcinol, 3,4-methylenedioxyphenol, 3,4-methylenedioxyaniline, or N-(2-hydroxyethyl)-3,4-methylenedioxyanilline, or combinations thereof.

7. The method of claim 6 wherein each compound of component B is present in the coloring composition in an amount of 0.03 mmol to 65 mmol, based on 100 g of the coloring composition as a whole.

8. The method of claim 1 wherein the coloring composition further comprises at least one activated carbonyl compound selected from the group consisting of isatin, 5-chloroisatin, 5-bromoisatin, 6-bromoisatin, 5-nitroisatin, N-hydroxymethylisatin, N-allylisatin, 5-isatinsulfonic acid Na salt, glutacoldehyde tetrabutylammonium salt, tribase aldehyde, malonaldehyde bis(dimethyl acetal), 4-hydroxy-3-methoxycinnanaldehyde, 1-piperidinomethylisatin, 1-diethylaminomethylisatin, glutaconaldehyde Na salt, 5-N-methylanilinopentadienyl, 2-chloro-3-hydroxymethylene-1-cyclohexene 1-aldehyde, N-(5-anilino-2,4-pentanedien-1-ylidene)anilinium chloride, trans-β-(2-furyl)acrolein, 2-nitro-1,3-indanedione, dehydroascorbic acid, 2-acetyl-1,3-cyclohexanedione, 7-dimethylamino-2,4,6-heptatrienylidene dimethylammonium perchlorate, 4-formyl-1-methylpyridinium benzenesulfonate, and combinations thereof.

9. The method of claim 1 wherein the coloring composition further comprises one or more compounds selected from 5,6-dihydroxyindole or its N-substituted $C_1$ to $C_4$ alkyl or $C_1$ to $C_4$ hydroxyalkyl derivatives, or 5,6-dihydroxyindoline or its N-substituted $C_1$ to $C_4$ alkyl or $C_1$–$C_4$-hydroxyalkyl derivatives or combinations thereof.

10. The method of claim 1 wherein the coloring composition further comprises one or more compounds selected from p-phenylenediamine, p-tolylenediamine, p-aminophenol, 4,4'-diaminodiphenylamine, 1,10-bis(2,5-diaminophenyl)-1,4,7,10-tetraoxydecane, 2,(2'-hydroxyethyl)-p-phenylenediamine, 2,6-dichloro-4-aminophenol, N,N-bis(2'-hydroxyethyl)-p-phenylenediamine, 3-methyl-4-aminophenol, 2-aminomethyl-4-aminophenol, 5-aminosalicylic acid, bis(2-hydroxy-5-aminophenyl)methane, or 2-(2,5-diaminophenoxy)ethanol, or combinations thereof.

11. The method of claim 1 wherein the coloring composition further comprises anionic surfactants, zwitterionic surfactants, nonionic surfactants, or combinations thereof.

12. The method of claim 1 wherein the coloring composition is combined with an enzyme containing system before the application of the coloring composition to the keratin fibers.

* * * * *

UNITED STATES PATENT AND TRADEMARK OFFICE
CERTIFICATE OF CORRECTION

PATENT NO. : 6,743,263 B1
DATED : June 1, 2004
INVENTOR(S) : Hoeffkes et al.

It is certified that error appears in the above-identified patent and that said Letters Patent is hereby corrected as shown below:

Column 16,
Line 29, delete "hydroxypyrimidine" and insert therefor -- dihydroxypyrimidine --.
Line 51, delete "methylenedioxyanillne" and insert therefor -- methylenedioxyaniline --.

Signed and Sealed this

Twenty-third Day of November, 2004

JON W. DUDAS
*Director of the United States Patent and Trademark Office*